United States Patent [19]

Zimmerli

[11] Patent Number: 5,117,849
[45] Date of Patent: Jun. 2, 1992

[54] CONTACT LENS CARE SYSTEM

[75] Inventor: Edwin Zimmerli, Uetikon, Switzerland

[73] Assignee: Lensmatic AG, Switzerland

[21] Appl. No.: 634,212

[22] PCT Filed: Mar. 30, 1990

[86] PCT No.: PCT/CH90/00083

§ 371 Date: Jan. 29, 1991

§ 102(e) Date: Jan. 29, 1991

[87] PCT Pub. No.: WO90/11785

PCT Pub. Date: Oct. 18, 1990

[30] Foreign Application Priority Data

Apr. 5, 1989 [CH] Switzerland ............... 1261/89

[51] Int. Cl.⁵ .......................................... B08B 3/06
[52] U.S. Cl. .......................... 134/57 R; 134/84; 134/142; 134/200; 134/901
[58] Field of Search ............ 134/200, 57 R, 56 R, 134/76, 84, 142, 901

[56] References Cited

U.S. PATENT DOCUMENTS

| | | | |
|---|---|---|---|
| 2,348,631 | 5/1944 | Keehnel | 134/77 X |
| 2,678,052 | 5/1954 | Moreland | 134/77 |
| 2,871,807 | 2/1959 | Lanzetter | 134/113 X |
| 2,886,046 | 5/1959 | Du Gal | 134/117 |
| 2,979,063 | 4/1961 | Hilton | 134/77 |
| 3,203,434 | 8/1965 | Kipp et al. | 134/77 X |
| 3,604,436 | 9/1971 | Lipshaw | 134/76 |
| 4,381,285 | 4/1983 | Wittenberg . | |
| 4,582,076 | 4/1986 | Prat | 134/901 X |
| 4,616,306 | 10/1986 | Kuzma et al. | 364/140 |

FOREIGN PATENT DOCUMENTS 0218539 9/1986 European Pat. Off. .
1429986 3/1976 United Kingdom ............ 134/78

*Primary Examiner*—Frankie L. Stinson
*Attorney, Agent, or Firm*—Speckman & Pauley

[57] ABSTRACT

An apparatus having a casing and a rotating cover with baskets to hold the contact lenses which are to be cleaned. The rotating cover is set on the casing with a guide rod. The contact lenses are first lowered into a tub in the casing containing a cleaning and disinfecting solution. After an adjustable amount of time, the rotating cover is pushed up by a push rod. The tip of the push rod is guided down a helical groove, thus rotating the cover 180°. At the end of its path, the push rod ends in a hole of the casing and the contact lenses are thus lowered into the tube containing the neutralization solution.

12 Claims, 2 Drawing Sheets

CONTACT LENS CARE SYSTEM

BACKGROUND OF THE INVENTION

The present invention is an apparatus designed to facilitate the chemical cleaning of contact lenses with two liquids. Systems that use two different liquids are referred to as two-step care systems. Such systems are based on use of hydrogen peroxide. In a first step, the disinfection and a certain amount of cleaning of the contact lenses are carried out with hydrogen peroxide-based solution. The second step is the neutralization of the contact lenses. This is done by replacing the hydrogen peroxide solution by a second, saline solution. Such two-step systems therefore usually have three elements. The first element is a plastic container with a basket or holder for the contact lenses built into the lid of the container. Second is a bottle holding the disinfecting and cleaning (hydrogen peroxide) solution for the lenses. Third is the bottle containing the solution for the second step, the neutralization and storage of the lenses. The neutralization solution is a physiological saline solution with a pH adjusted to that of natural tears.

The two-step system begins by placing the contact lenses in the basket attached to the lid of the plastic treatment and storage container. The container is partially filled with the disinfecting solution and the lid is replaced on the container, thus immersing the lenses in the solution. This first step lasts a specified amount of time, usually about 20 minutes. At the end of this first step of the treatment, the disinfecting solution is discarded and replaced by the neutralization solution, and the lid holding the contact lenses is replaced on the container. This neutralization step lasts a minimal recommended amount of time, in order to ensure a good subsequent wear comfort of the lenses. These steps must be followed very closely to avoid redness or infection of the eyes and/or damage to the contact lenses. Many types of contact lenses must be thus maintained daily. For practical reasons, this daily care is usually performed shortly before bedtime, when the wearer of the lenses no longer needs them. It is not uncommon for the wearer to forget to change the solutions, to fall asleep during the treatment time or even to avoid following exactly the recommended care directions. If the neutralization step is forgotten, or if the minimal time for neutralization is not achieved, the remaining hydrogen peroxide in the contact lenses can cause a very unpleasant buring sensation in the eyes and have serious and deleterious effects on the health of the eyes. The consequences can range from a slight irritation of the eyes to long-term damage of the cornea.

SUMMARY OF THE INVENTION

One object of the invention is thus to provide an automatic device for two-step contact lens care systems that performs the disinfection, the cleaning, and the neutralization steps without, requiring the intervention of the user.

The above object of the invention is achieved with an apparatus for the two-step care of contact lenses having a casing with two tubs holding the two solutions of the care system and a mobile basket holding the contact lenses, which is automatically and successively dipped in the disinfecting and neutralization solutions for the prescribed amount of time.

BRIEF DESCRIPTION OF THE DRAWINGS

Features and advantages of the invention are described in the specification and claims. The accompanying drawings illustrate one preferred embodiment of the invention, and together with the following description, explain the design and operation of the apparatus.

DESCRIPTION OF PREFERRED EMBODIMENT

Figure 1:
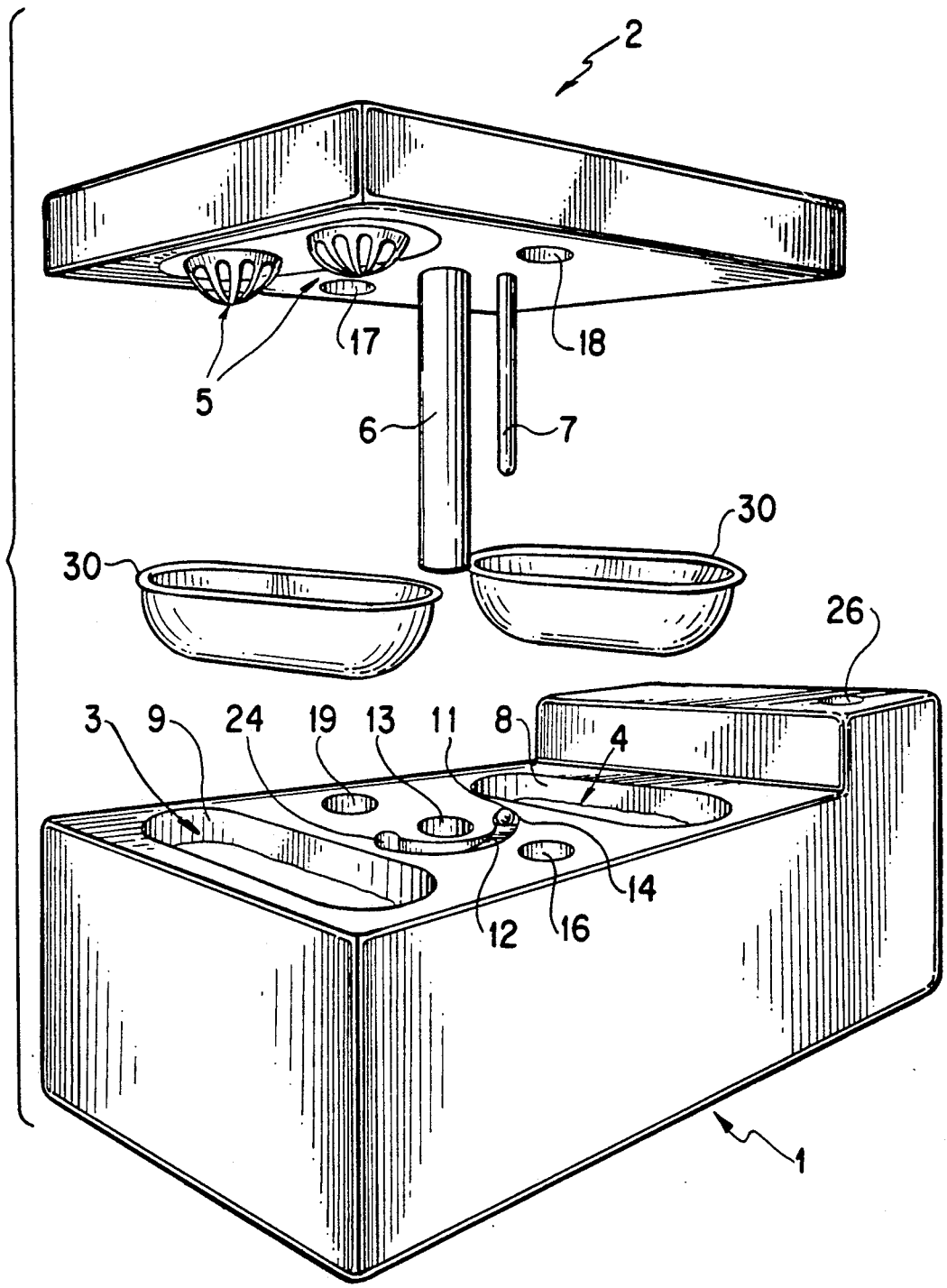
FIG. 1 shows a perspective view of the contact lens care apparatus with the cover removed.

The apparatus according to the invention as shown in FIG. 1 comprises a casing 1 containing a tub 9 for the cleaning and disinfecting solution 3, a tub 8 for the neutralization solution 4, and a rotating cover 2 with the basket 5 holding the contact lenses attached on its underside. This holder basket 5 can be removeable or hinged at the rotating cover 2, to facilitate the removal of the contact lenses. The lenses are placed in the baskets 5 while the baskets 5 are in the open position. The basket 5 is then closed and snapped locked against the rotating cover 2. The rotating cover 2 is attached to the casing by a guide rod 6 which sits in a bearing 13 in the casing 1. The rod 6 can be displaced axially and rotated within the bearing 13. The two tubs 8 and 9 are an integral part of the casing 1 and are located symmetrically on either side of the bearing 13. The actual containers holding the solutions can of course be designed as removable inserts 30 that would be placed in the tubs 8 and 9 in the casing 1. A modular design would present the advantage of being easier to clean, as the inserts could be removed and sterlized in boiling water. A recommended material for these insert is a flexible, rubbery, commerically available plastic such as Lupolen 1810H. The edges of the inserts are formed into a lip that rests on the edge of the tubs 8 and 9. When the rotating cover 2 is lowered onto and locked on the casing 1, the lip of the inserts act as a seal that prevents leaks and spills of the lens care solutions if the casing 1 should be tipped or knocked over. This makes the apparatus ideal for travels. One or two wedge-shaped latches (not shown) can be integrated in the cover 2 to lock the latter firmly onto the casing 1 and thus seal the inserts holding the solutions during transportation. Two permanent magnets 17 and 18 are built into the rotating cover 2. These two magnets interact with the metal cores 16 and 19 located in the casing 1 as is described in the following. Next to the guide rod 6 of the rotating cover 2, and parallel to it, is a small push rod 7. Depending on the position of the rotating cover 2 in relation to the casing 1, the push rod 7 fits into one of two holes 14 or 24 when the cover 2 is lowered onto the casing 1. The one hole 14 is equipped with a ball bearing 11 that sits on a compression spring 10. A groove 12, which is concentric with the central bearing 13, leads from the top of this first hole 14 to the bottom of the other hole 24 in a helical path.

Figure 2:
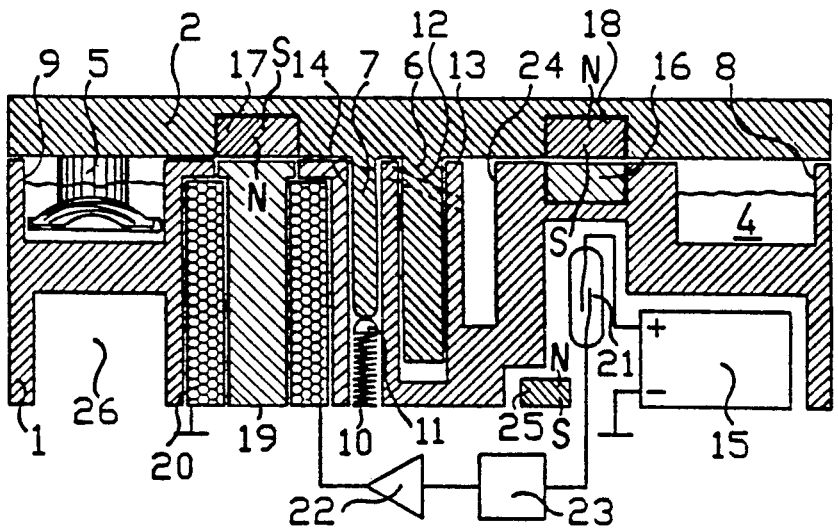
FIG. 2 is a schematic representation of the mechanism, the power supply, and the electrical control of the apparatus; and apparatus is in the first phase of operation, with the lenses immersed in the cleaning and disinfecting solution.
Figure 3:
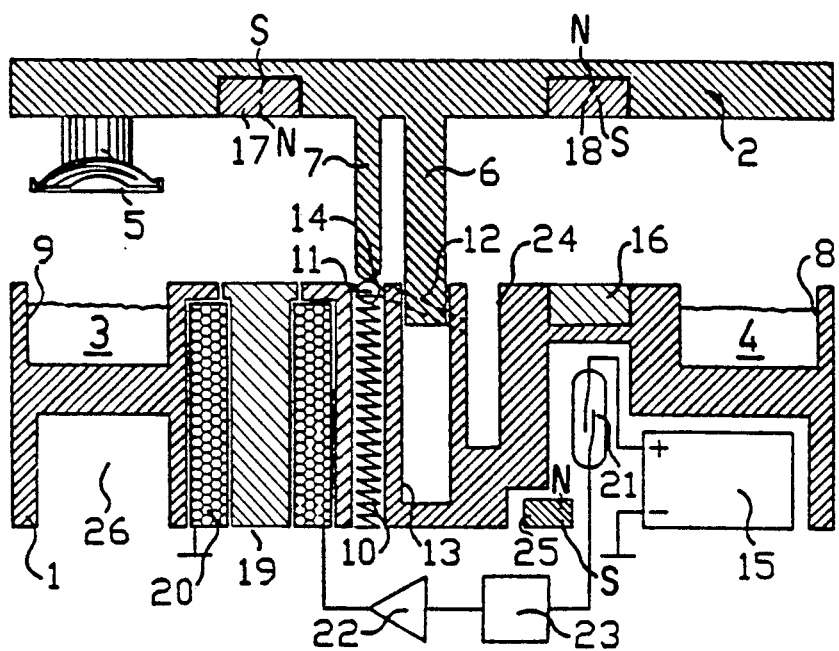
FIG. 3 is a schematic representation of the mechanism, the power supply, and the electrical control of the apparatus; the apparatus is in the intermediate phase, just before rotation of the cover.
Figure 4:
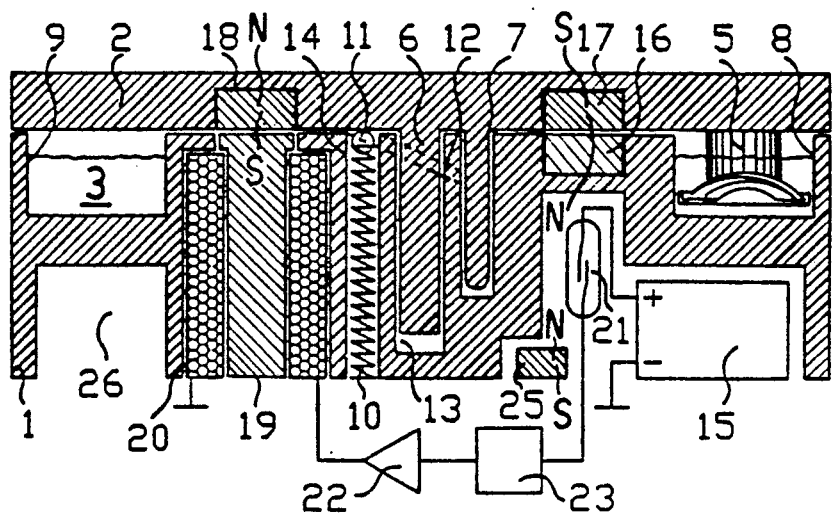
FIG. 4 is a schematic representation of the mechanism, the power supply, and the electrical control of the apparatus; the apparatus is in the final phase, with the lenses in the neutralization solution.

The schematic diagrams in FIGS. 2, 3, and 4 illustrate, in cross section, the operation of the apparatus, and the function of the individual elements just described. The tub 9, or the insert placed in it, contains the cleaning and disinfecting solution 3; the other tub 8, or the insert placed in it, contains the neutralization solution 4. FIG. 4 shows the apparatus in its final cycle, in which the contact lenses, or at least the holder baskets 5 are immersed in the neutralization solution. This end position is also the starting position and the position of the cover 2 when the apparatus is not in use.

To use the appartus, starting in the position shown in FIG. 4, the rotating cover 2 is pulled out of the bearing 13, and the contact lenses are placed in the basket 5. The cover 2 is then replaced on the casing 1 with the guide rod 6 inserted in the bearing 13, as shown in FIG. 2. In this position, the push rod 7 fits into hole 14 when the cover 2 is pressed down, thus pushing down and tensing the release mechanism which comprises a spring 10 and a ball bearing 11. As can be seen in FIG. 2, the basket 5 holding the contact lenses is then immersed in the tub 9 containing the cleaning and disinfecting solution. Pushing down the rotating cover 2 in the position shown in FIGS. 2 also sets in motion a timed trigger mechanism. This electrical trigger mechanism in shown schematically in FIGS. 2 to 4; its operation is described as follows. Two permanent magnets 17, 18 are situated in the cover 2; their North (N) and South (S) poles, as seen in FIGS. 2 to 4, are oriented in opposite directions. When the cover 2 is pressed down in the position shown in FIG. 2, these permanent magnets 17, 18 are attracted to the metal cores 16. 19 and thus act against the force of the compressed spring 10. The one magnet 18 simultaneously switches on a Reed switch 21, thus activating the circuit powered by battery 15. This starts a timer 23 which can be set according to the needed treatment time.

At the end of the set period, the amplifier 22 is switched on, thus powering the solenoid coil 20 and the core 19, which is flush with the top of the casing 1. The magnetic field thus created repels the permanent magnet 17. The other magnet 18 alone is not strong enough to counteract the force of the compressed spring 10, and the release mechanism is activated. The spring 10 topped by the ball bearing 11 pushing the cover 2 upward, via the push rod 7. In the process, the basket 5 holding the contact lenses is lifted out of the cleaning and disinfecting solution. At the top of hold 14, the tip of the push rod 7 slides off the ball bearing 11 and, under the weight of the rotating cover 2, down the helical groove 12 (see also FIG. 1) into the other hole 24. This causes the rotating cover 2 to turn 180°, to lower itself back onto the casing 1 in the position shown in FIG. 4. The basket 5 holding the contact lenses is thus lowered into the neutralization solution contained in the other tub 8. A catalyst, e.g. a platinum-covered disk, can be placed in this second tub 8, to break up the remaining hydrogen peroxide fractions on the lenses, thus leaving the lenses in a mild saline solution. The slight pressure or vaccuum in the bearing 13 during the automatic lowering or raising of the cover 2 dampens the up-and-down motion of the rotating cover 2.

A permanent magnet 25, placed under the Reed switch 21, and the one in the cover 17, magnetically tense the switch and thus prevent it from switching on. The Reed switch 21, located under the metal core 16 and parallel to the coil 20, is only switched on when the cover 2 is pressed down in the position shown in FIG. 2, where the spring 10 is compressed. The two magnets 18, 25 which are then aligned with the switch have their polarity oriented in the same direction, and the resulting magnetic field acitvates the switch. As soon as the timer-controlled release takes place and the one magnet 18 moves away, the magnetic field decreases in intensity sufficiently to deactivate the Reed switch 21. When the cover has rotated and magnet 17 is in contact with the core 16, the two opposing magnetic fields (from magnets 17 and 25) cancel each other out and the switch stays in the off position.

The apparatus according to the invention operates on a commerical, 9 Volt alkaline battery 15. When the battery 15 runs too low, the magnetic field induced by the coil 20 is no longer strong enough to neutralize the attraction between the magnet 17 and the core 19 sufficiently for the spring 10 to push the cover 2 up. The cover stays in place, with the contact lenses remaining in the cleaning and disinfecting solution, instead of rotating into the position for neutralization of the lenses. In order to warn the user of this condition, the apparatus is equipped with a warning light 26 on the casing 1. This light can be a commerical, integrated "low battery indicator" circuit, which switches the current automatically to a light-emitting diode 26 when the voltage on the battery 15 falls below a certain value. The user is thus informed that the battery 15 needs to be changed before the apparatus can further be used properly. Of course, the apparatus can be powered by rechargeable batteries of the NiCad type. or off a wall plug, over a transformer.

I claim:

1. Apparatus for a two-step cleaning of a plurality of contact lenses, the apparatus comprising:
   a casing (1) with two tubs (8, 9) designed to receive two different lens-care solutions (3, 4);
   a rotating cover (2) having a basket (5) which can be successively lowered into the two tubs (8, 9), said rotating cover mounted on a guide rod (6) displaceable axially and rotatably within a bearing (13) positioned between the two tubs (8, 9) in the casing (1);
   means for automatically moving the basket (5) from one tub (9) of the two tubs (8, 9) to another tub (8) of the two tubs (8, 9);
   said rotating cover (2) having a push rod (7) set parallel to the guide rod (6); and
   said casing (1) having two holes (14, 24) into which the push rod (7) can be inserted, said holes (14, 24) being connected by a helical groove (12) which is concentric with the bearing (13) and which leads from the top of one hole (14) of the two holes (14, 24) to the bottom of another hole (24) of the two holes (14, 24).

2. Apparatus according to claim 1, further comprising a ball bearing (11) positioned on top of a compression spring (10) within the one hole (14), and magnetic means for holding the rotating cover (2) down on the casing (1) and for holding the spring (10) in a compressed position via the push rod (7).

3. Apparatus according to claim 2, wherein the magnetic means comprises a plurality of permanent magnets (17, 18) mounted in the cover (2), at least one iron core (16) mounted in the casing (1), and at least one electromagnet (19, 20) driven by an electronically controlled power supply.

4. Apparatus according to claim 3, wherein the permanent magnets (17, 18) are fixed in the rotating cover (2), one permanent magnet of the permanent magnets (17, 18) has a North pole oriented toward the casing (1), another permanent magnet of the permanent magnets (17, 18) has a South pole oriented toward the casing (1), the, permanent magnets (17, 18) face two corresponding said iron cores (16, 19), and one iron core (19) of the iron cores having a coil (20) forming an electromagnet (19, 20) fixed in the casing (1) when the rotating cover (2) is in its lowered position, with the push rod (7) holding the spring (10) in a compressed state.

5. Apparatus according to claim 4, wherein the electronically controlled power supply comprises a contactless Reed switch (21), an integrated circuit acting as a timer (23), and an amplifier (22), the Reed switch (21) is located in the casing (1) between another iron core (16) of the iron cores and a second permanent magnet (25) so that North poles of the permanent magnets (18, 25) on either side of the Reed switch (21) are oriented in opposing directions when the rotating cover (2) is in a lowered position, with the push rod (7) holding the spring (10) in a compressed state.

6. Apparatus according to claim 5, further comprising flexible, rubbery inserts positioned in the tubs (8, 9) of the casing (1) and having edges formed into a lip that rests on a tub edge of the tubs (8, 9) for sealing the inserts against the rotating cover (2) when the rotating cover (2) is lowered onto and locked on the casing (1).

7. Apparatus according to claim 6, further comprising sliding locks arranged on the rotating lid (2) or on the casing (1), the sliding locks pressing and locking the rotating lid (2) in a lowered position onto the casing (1).

8. Apparatus according to claim 7, wherein the casing (1) is equipped with a warning light (26) which is lit when there is relatively low battery (15) power.

9. Apparatus according to claim 8, further comprising a platinum coated catalyst located in one of the tub (8) and the insert holding the neutralization solution.

10. Apparatus according to claim 3, wherein the electronically controlled power supply comprises a contactless Reed switch (21), an integrated circuit acting as a timer (23), and an amplifier (22), the Reed switch (21) is located in the casing (1) between one iron core (16) of the iron cores and a second permanent magnet (25) so that North poles of the permanent magnets (18, 25) on either side of the Reed switch (21) are oriented in opposing directions when the rotating cover (2) is in a lowered position, with the push rod (7) holding the spring (10) in a compressed state.

11. Apparatus according to claim 1, further comprising flexible, rubbery inserts positioned in the tubs (8, 9) of the casing (1) and having edges formed into a lip that rests on a tub edge of the tubs (8, 9) for sealing the inserts against the rotating cover (2) when the rotating cover (2) is lowered onto and locked on the casing (1).

12. Apparatus according to claim 1, further comprising a platinum coated catalyst located in one of the tub (8) and the insert holding the neutralization solution.

* * * * *